(12) United States Patent
Iishi et al.

(10) Patent No.: US 6,376,668 B1
(45) Date of Patent: Apr. 23, 2002

(54) PROCESS FOR PREPARING PYRIDINEMETHANOL COMPOUNDS

(75) Inventors: Eiichi Iishi, Osaka; Kanami Yoshikawa, Kashiba, both of (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/706,803

(22) Filed: Nov. 7, 2000

Related U.S. Application Data (63) Continuation-in-part of application No. PCT/JP00/05384, filed on Aug. 11, 2000.

(30) Foreign Application Priority Data

Dec. 13, 1999 (JP) ............................................. 11-353514

(51) Int. Cl.⁷ ...................... C07D 401/04; C07D 471/14
(52) U.S. Cl. ...................................... 544/360; 540/578
(58) Field of Search ............................ 544/360; 540/578

(56) References Cited

U.S. PATENT DOCUMENTS

| | | | |
|---|---|---|---|
| 4,062,848 A | | 12/1977 | van der Burg |
| 5,196,532 A | * | 3/1993 | Wuest et al. ................ 544/144 |

FOREIGN PATENT DOCUMENTS

| | | |
|---|---|---|
| GB | 1543171 | 3/1979 |

OTHER PUBLICATIONS

F. M. Kaspersen et al., *Journal of Labelled Compounds and Radiopharmaceuticals*, vol. 27, No. 9, pp. 1055–1068 (1989).

* cited by examiner

*Primary Examiner*—Emily Bernhardt
(74) *Attorney, Agent, or Firm*—Birch, Stewart, Kolasch & Birch, LLP (57) ABSTRACT

A pyridinemethanol compound is an important intermediate for a mirtazapine which is useful as an antidepressant. The pyridinemethanol compound is obtained by reducing potassium pyridinecarboxylate represented by the formula (I):

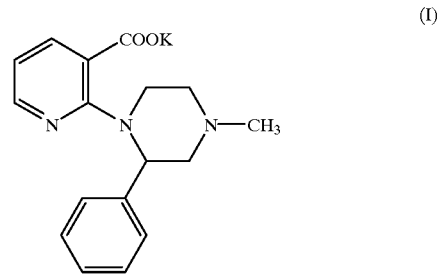

with a metal hydride.

20 Claims, 2 Drawing Sheets

PROCESS FOR PREPARING PYRIDINEMETHANOL COMPOUNDS

This application is a continuation-in-part application of PCT/JP00/05384, filed Aug. 11, 2000 the entire contents of which are incorporated herein by reference.

BACKGROUND OF THE INVENTION

1. Field of the Invention

The present invention relates to a pyridinemethanol compound. More specifically, the present invention relates to a process capable of simply and industrially preparing a pyridinemethanol compound, which is an important intermediate for mirtazapine which is useful as an antidepressant, and a process for preparing mirtazapine using the pyridinemethanol compound.

2. Discussion of the Related Art

Conventionally, as a process for preparing a pyridinemethanol compound represented by the formula (II):

there has been proposed a process comprising reducing a pyridinecarboxylic acid represented by the formula (IV):

using lithium aluminum hydride (U.S. Pat. No. 4,062,848).

However, there are some defects in this process that the process is not economical because it is required to use an expensive reagent lithium aluminum hydride in a large amount as much as 8 times equivalent based on pyridinecarboxylic acid.

Also, in this process, pyridinecarboxylic acid is obtained by dissolving a pyridinecarbonitrile compound in ethanol, hydrolyzing the pyridinecarbonitrile compound with potassium hydroxide under reflux for 24 hours, and thereafter adding an acid thereto to liberate pyridinecarboxylic acid. However, there are some defects in this process that its production efficiency is poor because the hydrolysis requires a long period of time and there is a necessity to liberate the resulting pyridinecarboxylic acid.

In addition, conventionally, as a process for preparing mirtazapine, there has been known a process as disclosed in U.S. Pat. No. 4,062,848.

However, there are some defects in the process that stirring is difficult because concentrated sulfuric acid is added in a thin stream to the pyridinemethanol compound, so that the reaction control would be difficult, and that a large amount of an aqueous ammonia is required in order to make the reaction mixture alkaline with the aqueous ammonia. In addition, there are some defects in the process that even the impurities are extracted because the reaction product is extracted with chloroform, and that mirtazapine having a high purity cannot be obtained because crystallization is inhibited during the crystallization from an ether.

The present invention has been accomplished in view of the prior art described above. An object of the present invention is to provide a process capable of economically and efficiently preparing a pyridinemethanol compound.

Another object of the present invention is to provide a process capable of efficiently preparing mirtazapine from the above-mentioned pyridinemethanol compound on an industrial scale, to give mirtazapine having a high purity.

These and other objects of the present invention will be apparent from the following description.

SUMMARY OF THE INVENTION

According to the present invention, there are provided:

(1) a process for preparing a pyridinemethanol compound represented by the formula (II):

comprising reducing potassium pyridinecarboxylate represented by the formula (I):

with a metal hydride; and (2) a process for preparing mirtazapine comprising adding a pyridinemethanol compound represented by the formula (II):

to sulfuric acid.

DETAILED DESCRIPTION OF THE INVENTION

The potassium pyridinecarboxylate represented by the formula (I):

can be easily prepared by using a pyridinecarbonitrile compound represented by the formula (III):

or a salt thereof as a starting material, and reacting the pyridinecarbonitrile compound or a salt thereof with potassium hydroxide in butanol.

As described above, one of the great features of the present invention resides in that the pyridinecarbonitrile compound or a salt thereof is reacted with potassium hydroxide in butanol.

Conventionally, there is exhibited an especially remarkably excellent effect that the reaction time can be surprisingly shortened for about not less than 15 hours when both of the compounds are reacted in butanol, while a reaction time of 24 hours or so is required when ethanol is used.

Furthermore, there is exhibited an especially remarkably excellent effect that potassium pyridinecarboxylate formed by the reaction of the pyridinecarbonitrile compound or a salt thereof with potassium hydroxide can be easily and efficiently extracted from the reaction solution because butanol is used in the present invention.

The pyridinecarbonitrile compound is concretely 2-(4-methyl-2-phenylpiperazin-1-yl)pyridine-3-carbonitrile. As the salt of the pyridinecarbonitrile compound, there can be cited, for instance, oxalates, hydrochlorides, methanesulfonates, and the like of 2-(4-methyl-2-phenylpiperazin-1-yl)pyridine-3-carbonitrile.

As the butanol, there can be cited, for instance, 1-butanol, isobutanol, sec-butanol, and mixed solvents thereof. Among these butanols, 1-butanol is preferable. The amount of the butanol is not limited to specified ones. It is preferable that the amount is usually 300 to 800 parts by weight or so, preferably 400 to 600 parts by weight or so based on 100 parts by weight of the pyridinecarbonitrile compound or a salt thereof, from the viewpoints of shortening the reaction time and improving the volume efficiency.

As the form of potassium hydroxide, there can be usually cited flaky, granular, and the like. Among them, flaky is preferable from the viewpoint of solubility.

It is preferable that the amount of potassium hydroxide is usually 7 to 14 moles, preferably 8 to 12 moles per one mole of the pyridinecarbonitrile compound, from the viewpoint of shortening the reaction time. When the salt of the pyridinecarbonitrile compound is used, it is preferable that potassium hydroxide is further added in an amount required for neutralization because potassium hydroxide is consumed during the neutralization of the salt.

It is preferable that the reaction temperature of the pyridinecarbonitrile compound or a salt thereof with potassium hydroxide is usually 120° to 145° C., preferably 120° to 140° C., more preferably 130° to 140° C., from the viewpoint of shortening the reaction time. As described above, as to the temperature of the reaction of the pyridinecarbonitirle compound or a salt thereof with potassium hydroxide, butanol does not boil even at a temperature of not lower than the boiling point of the butanol (e.g. boiling point of 1-butanol: about 118° C.) under atmospheric pressure, since potassium hydroxide is used. Therefore, the reaction of both compounds can be efficiently carried out.

It is preferable that the reaction is carried out, for instance, in an atmosphere of an inert gas such as nitrogen gas or argon gas, from the viewpoint of preventing coloration of the resulting potassium pyridinecarboxylate represented by the formula (I).

The period of time required for the reaction of the pyridinecarbonitrile compound or a salt thereof with potassium hydroxide cannot be absolutely determined, because it differs depending upon the reaction temperature of both compounds. The period of time is usually 5 to 10 hours or so.

The termination of the reaction can be confirmed by the disappearance of the starting materials using, for instance, high-performance liquid chromatography (hereinafter referred to as "HPLC") or the like.

The thus obtained potassium pyridinecarboxylate represented by the formula (I) is specifically potassium 2-(4-methyl-2-phenylpiperazin-1-yl)pyridine-3-carboxylate.

Next, potassium hydroxide in the reaction solution can be removed by adding water to the reaction solution, and allowing the reaction solution to separate into an organic layer and an aqueous layer, thereby transferring the potassium hydroxide contained in the reaction solution to the aqueous layer.

The amount of water used in the separation is not limited to specified ones. It is preferable that the amount of water is usually 400 to 600 parts by weight or so based on 100 parts by weight of the pyridinecarbonitrile compound or a salt thereof, from the viewpoints of improving separability and volume efficiency.

It is preferable that the temperature during the separation is 30° to 60° C., from the viewpoints of preventing precipitation of alkalis and improving extraction efficiency.

The potassium pyridinecarboxylate can be collected by further extracting the aqueous layer with a butanol after the separation, allowing to separate into a butanol layer and an aqueous layer, and transferring the potassium pyridinecarboxylate existing in the aqueous layer to the butanol layer.

Next, the above-mentioned organic layer and butanol layer can be combined, and the butanol and water can be distilled away from the resulting liquid mixture to concentrate the liquid mixture.

The butanol and water can be distilled away under reduced pressure. It is preferable that the pressure during the distillation is usually 1 to 20 kPa, from the viewpoint of increasing the rate for distillation. In addition, it is desired that the temperature during the distillation of the butanol and water is usually 30° to 80° C., preferably 40° to 60° C., from the viewpoint of increasing the rate for distillation.

The amount of the butanol and water distilled away is not limited to specified ones. It is preferable that the amount is usually 400 to 900 parts by weight, preferably 600 to 900 parts by weight based on 100 parts by weight of the pyridinecarbonitrile compound or a salt thereof, from the viewpoint of sufficiently distilling away water.

Next, in order to further distill away moisture and the butanol remaining in the above-mentioned liquid mixture, it is preferable that the liquid mixture is mixed with a hydrocarbon, and the resulting reaction solution is heated to azeotropically distill away the butanol and water.

As the hydrocarbon, there can be cited, for instance, toluene, xylene, benzene, and the like. Among them, xylene is preferable.

The amount of the hydrocarbon differs depending upon the amount of the butanol and water contained in the mixed solution. It is desired that the amount is usually 100 to 600 parts by weight, preferably 200 to 300 parts by weight based on 100 parts by weight of the pyridinecarbonitrile compound or a salt thereof, from the viewpoint of efficiently azeotropically distilling away.

It is desired that the temperature during the azeotropic distillation usually satisfies the internal temperature of 110° to 130° C., preferably 120° to 130° C., from the viewpoint of efficiently azeotropically distilling away.

It is preferable that the azeotropic distillation is carried out until the water content in the mixed solution attains to not more than 1% by weight, preferably not more than 0.5% by weight, when determined by Karl-Fischer method, from the viewpoint of efficiently progressing the subsequent reduction reaction step.

Since the hydrocarbon and the butanol are contained in the solution after the azeotropic distillation, it is preferable to distill away these solvents. The above distillation can be carried out by heating the reaction solution. In this case, it is desired that the heating temperature usually satisfies the internal temperature of 130° to 140° C., preferably 135° to 140° C., from the viewpoint of sufficiently distilling away the hydrocarbon and the butanol.

It is preferable that the amount of the hydrocarbon distilled away is usually 65 to 90% by weight or so, preferably 80 to 90% by weight or so of the amount of the hydrocarbon used, from the viewpoint of sufficiently distilling away the butanol.

The resulting potassium pyridinecarboxylate may be isolated. It is preferable that a one-pot reaction of directly reducing a concentrate is carried out. The pyridinemethanol compound represented by the formula (II):

(II)

can be prepared by reducing potassium pyridinecarboxylate with a metal hydride.

One of the great features of the present invention resides in that potassium pyridinecarboxylate is reduced with a metal hydride. The potassium pyridinecarboxylate has an excellent characteristic that it easily dissolves in an ether solvent such as tetrahydrofuran (hereinafter referred to as THF) which is used during the reduction. Therefore, the amount of the metal hydride which is used during reduction can be decreased, and at the same time the potassium pyridinecarboxylate can be easily reduced with the metal hydride.

During the reduction of the potassium pyridinecarboxylate with the metal hydride, the solution from which the hydrocarbon is distilled away obtained as mentioned above can be directly used. When the above solution is used, the pyridinemethanol compound can be directly and efficiently obtained without the isolation of the potassium pyridinecarboxylate.

In addition, in the present invention, there is employed not a conventional process of reducing the pyridinecarboxylic acid with lithium aluminum hydride, but a process of reducing the potassium pyridinecarboxylate with the metal hydride. In the case where this process is employed, there is taken in an excellent effect that the amount of the metal hydride can be remarkably decreased. As the metal hydride, there can be cited lithium aluminum hydride, bis(2-methoxyethoxy)aluminum sodium hydride, diisobutylaluminum hydride, and the like. Among them, lithium aluminum hydride can be favorably used.

During the reduction of the potassium pyridinecarboxylate with the metal hydride, there can be used a solution or suspension in which the metal hydride is previously dissolved or suspended in an organic solvent. As the organic solvent, there can be cited THF, diethyl ether, and the like. Among them, THF can be favorably used, from the viewpoint of easy handling.

In addition, when using a solution in which the above-mentioned hydrocarbon is distilled away, in order to efficiently reduce the potassium pyridinecarboxylate contained in the solution, it is preferable that the solution is previously diluted with the above-mentioned organic solvent. Among the above-mentioned organic solvents, THF can be favorably used.

It is desired that the total used amount of the organic solvents is usually 500 to 1200 parts by weight or so, preferably 700 to 900 parts by weight based on 100 parts by weight of the potassium pyridinecarboxylate, from the viewpoint of accelerating the reduction reaction.

In addition, it is preferable that the amount of the metal hydride is usually 2.5 to 5 moles, preferably 3 to 4 moles per one mole of the potassium pyridinecarboxylate, from the viewpoint of accelerating the reduction reaction.

It is preferable that the atmosphere during the reduction of the potassium pyridinecarboxylate is an inert gas atmosphere. As the inert gas, there can be cited, for instance, nitrogen gas, argon gas, and the like. Among them, nitrogen gas is preferable.

The reduction of the potassium pyridinecarboxylate can be easily carried out by, for instance, adding in a thin stream a dilute solution prepared by diluting with an organic solvent the above-mentioned solution in which the hydrocarbon is distilled away, to a solution or suspension prepared by dissolving or suspending a metal hydride in an organic solvent. During the reduction, it is preferable that each of the liquid temperatures of the solution and suspension, prepared by dissolving or suspending a metal hydride in an organic solvent, and the dilute solution is 10° to 50° C., preferably 15° to 35° C., from the viewpoint of efficiently progressing the reduction reaction.

The period of time required for the reduction reaction of the potassium pyridinecarboxylate cannot be absolutely determined because the period of time differs depending upon the amount of the potassium pyridinecarboxylate, the reaction temperature, and the like. The period of time is usually 1 to 6 hours or so.

The termination of the reaction can be confirmed by the disappearance of the potassium pyridinecarboxylate by, for instance, HPLC, or the like.

After the termination of the reaction, it is preferable that water is added in a thin stream to the reaction solution. It is desired that the amount of water is 90 to 110 parts by weight, preferably 95 to 100 parts by weight based on 100 parts by weight of the metal hydride. Since the reaction solution generates heat during the addition of water, it is preferable that the addition of water is carried out so that the liquid temperature of the reaction solution can be 0° to 20° C.

Next, an aqueous alkali is added in a thin stream to the reaction solution. As the alkali usable for the aqueous alkali, there can be cited alkali metal hydroxides such as sodium hydroxide and potassium hydroxide. Among them, sodium hydroxide is preferable. When the aqueous sodium hydroxide is used as an aqueous alkali, it is preferable that the concentration of sodium hydroxide is usually 20 to 25% by weight or so. It is desired that the amount of sodium hydroxide is usually 0.1 to 0.25 moles, preferably 0.15 to 0.2 moles per one mole of the metal hydride.

During the addition of the aqueous alkali in a thin stream, it is desired that the liquid temperature of the reaction solution is 0° to 30° C., preferably 0° to 15° C.

Next, in order to improve the slurry property of this reaction solution, it is preferable to add water thereto. It is desired that the amount of water is 200 to 500 parts by weight, preferably 250 to 400 parts by weight based on 100 parts by weight of the metal hydride. In addition, it is desired that the temperature during addition of water in a thin stream is 0° to 30° C., preferably 0° to 20° C.

In order to improve the filterability of a metal hydroxide formed from the metal hydride by hydrolysis, it is desired that the reaction solution is aged at 15° to 30° C. for 30 minutes to 4 hours, preferably at 20° to 25° C. for 1 to 2 hours.

Next, the reaction solution is filtered to collect the metal hydroxide by filtration. It is preferable that the liquid temperature of the reaction solution during the filtration is 15° to 25° C.

Since the desired compound, pyridinemethanol compound represented by the formula (II) remains in the collected metal hydroxide, it is preferable that the metal hydroxide is washed with a solvent such as THF. The amount of the solvent is not limited to specified ones. It is desired that the amount of the solvent is usually 500 to 3000 parts by weight, preferably 1000 to 2000 parts by weight based on 100 parts by weight of the metal hydride.

Next, THF and water are distilled away from the filtrate solution under atmospheric pressure until its internal temperature attains to about 110° C. It is preferable that its distillation amount is 60 to 90% by weight, preferably 65 to 80% by weight of the amount of the THF used in dissolving and reducing the potassium pyridinecarboxylate used.

Next, the pyridinemethanol compound is crystallized. It is preferable that the crystallization is carried out by adding heptane in a thin stream to a solution after distillation. The amount of heptane is not limited to specified ones, which may be usually the amount that can sufficiently crystallize the pyridinemethanol compound. It is desired that the amount of heptane is usually 50 to 300 parts by weight, preferably 90 to 200 parts by weight based on 100 parts by weight of the potassium pyridinecarboxylate. It is desired that the temperature during the addition of heptane in a thin stream is 40° to 90° C., preferably 50° to 70° C. The period of time for the addition in a thin stream may depend upon the amount of the starting materials. The period of time is usually 1 to 2 hours.

In addition, during the crystallization, seed crystals may be added. The seed crystals may be added at the beginning of the addition of heptane in a thin stream or in the course of addition in a thin stream. It is preferable that the seed crystals are added at the beginning of the addition of heptane in a thin stream. The amount of the seed crystals is not limited to specified ones. It is preferable that the amount is usually 0.5 to 5% by weight or so of the potassium pyridinecarboxylate. The temperature during the addition of the seed crystals may be 50° to 65° C. or so.

After the termination of the addition of heptane in a thin stream, it is preferable that aging of the slurry mixture is carried out with cooling. It is preferable that the aging with cooling is carried out at 0° to 5° C. for 30 minutes to 2 hours.

Thereafter, the slurry mixture is filtered, and the residue is washed. The filtration temperature may be 0° to 5° C. Washing can be carried out by using a mixed solvent prepared by mixing an equal volume of toluene and heptane, and cooling to 0° to 5° C. The amount of the mixed solvent is not limited to specified ones. It is preferable that the amount is usually 100 to 150 parts by volume based on 100 parts by weight of the potassium pyridinecarboxylate.

It is preferable that the pyridinemethanol compound is usually dried at 50° to 60° C. under reduced pressure of 0.6 to 14 kPa.

Figure 1:
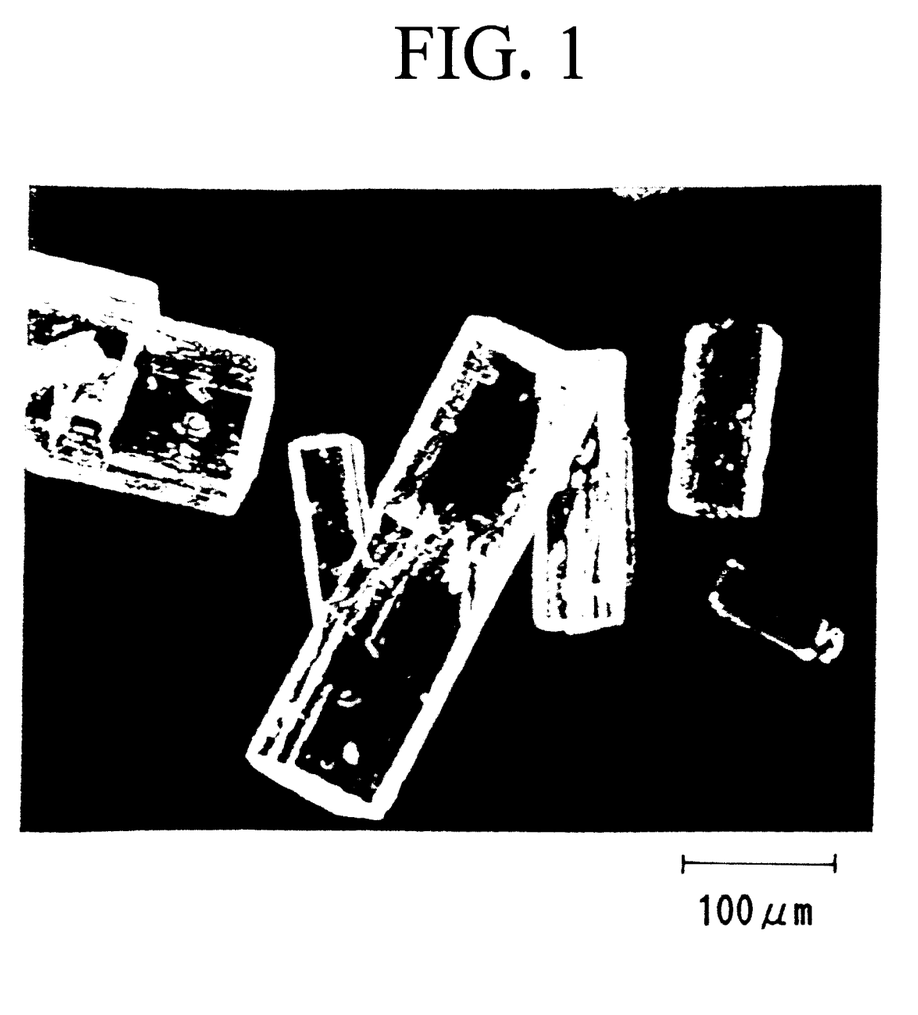
FIG. 1 is a microphotograph of 2-(4-methyl-2-phenylpiperazin-1-yl)pyridine-3-methanol obtained in Example 4.

The pyridinemethanol compound has a rod-like crystal form as shown in FIG. 1, and an average particle diameter is 75 to 90 μm. Therefore, the pyridinemethanol compound has a desired crystal form, from the viewpoints of filtration, drying, and the like.

In addition, in the present invention, mirtazapine can be prepared by using the pyridinemethanol compound. More specifically, mirtazapine can be prepared by adding the pyridinemethanol compound to sulfuric acid.

It is preferable that the atmosphere during the addition of the pyridinemethanol compound to sulfuric acid is, for instance, an atmosphere of an inert gas such as nitrogen gas or argon gas.

As sulfuric acid, there can be favorably used a concentrated sulfuric acid of which concentration is 97 to 99%. It is desired that the temperature of sulfuric acid during the addition of the pyridinemethanol compound is 0° to 40° C., preferably 5° to 35° C., from the viewpoints of suppressing heat generation and suppressing the formation of impurities in a tarred state.

When the pyridinemethanol compound is added to sulfuric acid, it is preferable that the pyridinemethanol compound is added in divided portions to sulfuric acid, from the viewpoint of efficiently progressing the reaction. For instance, it is preferable that the pyridinemethanol compound is added in 5 to 20 divided portions to sulfuric acid.

It is desired that the amount of sulfuric acid is usually 300 to 400 parts by weight, preferably 350 to 400 parts by weight based on 100 parts by weight of the pyridinemethanol compound.

After the addition of the pyridinemethanol compound to sulfuric acid, it is preferable that the mixture is stirred at a temperature of 30° to 40° C. or so for 7 to 10 hours or so, in order to accelerate the reaction.

Thus, the pyridinemethanol compound is subjected to dehydration and ring closure, and the end point of the ring closure reaction can be confirmed by HPLC.

Next, it is preferable to add water to the resulting reaction solution by means such as addition of water in a thin stream, in order to decrease the concentration of sulfuric acid. It is preferable that the amount of water is 100 to 200 parts by weight or so based on 100 parts by weight of the reaction solution, from the viewpoint of operability. In addition, it is preferable that the liquid temperature of the reaction solution during the addition of water is 0° to 30° C. or so, from the viewpoints of suppressing heat generation and suppressing formation of impurities (tarred product).

Next, it is preferable that an aqueous alkali is added to the reaction solution for the purpose of neutralization. As the alkali, there can be cited, for instance, sodium hydroxide, potassium hydroxide, sodium carbonate, and the like. Among them, sodium hydroxide is preferable. It is desired that the concentration of the alkali hydroxide in the aqueous alkali is 20 to 25% by weight, from the viewpoint of operability. It is desired that the amount of the aqueous alkali hydroxide is 50 to 250 parts by weight, preferably 80 to 110 parts by weight based on 100 parts by weight of the reaction solution.

After the addition of the aqueous alkali hydroxide, it is desired that the pH of its solution is adjusted to 1 to 3, preferably to 1 to 2, in order not to precipitate crystals. The adjustment of the pH can be carried out by, for instance, adding sodium hydroxide or the like to the solution.

After the adjustment of the pH, it is preferable that decolorizing carbon is added to its solution for decolorizing the solution.

Next, mirtazapine can be extracted by filtering this solution, and adding toluene to the filtrate as occasion demands.

It is desired that the amount of toluene is 100 to 400 parts by weight, preferably 200 to 300 parts by weight based on 100 parts by weight of the pyridinemethanol compound, from the viewpoint of increasing yields. After the addition of toluene, it is preferable that an alkali is added to the mixture at a temperature of 20° to 50° C. to adjust its pH of 8 to 12 in order to completely end the neutralization. As the alkali, there can be cited, for instance, an aqueous sodium hydroxide and the like.

Next, it is preferable that this solution is heated to a temperature of 75° to 80° C. in order to dissolve the crystals, thereby improving separability.

When this solution is allowed to stand, the mixture is separated into two layers. Among them, heptane is added to the organic layer in order to crystallize mirtazapine. It is desired that the temperature during the addition of heptane is 40° to 70° C., preferably 50° to 60° C., from the viewpoint of improving filterability. It is desired that the amount of heptane is 50 to 200 parts by weight, preferably 70 to 100 parts by weight based on 100 parts by weight of toluene, from the viewpoint of increasing yields. In addition, during the addition of heptane, it is preferable that the heptane is added in a thin stream. It is desired that its addition in a thin stream is carried out over a period of 1 to 4 hours, preferably 1 to 2 hours.

Next, it is preferable that the resulting solution is gradually cooled to a temperature of 0 to 5° C. over a period of 1 to 5 hours, preferably 2 to 3 hours, in order to form a uniform crystal and to increase yields.

Thus, the mirtazapine can be crystallized, and the crystals may be washed with a mixed solvent, prepared by, for instance, mixing toluene with heptane, and cooling the mixture to 0° to 5° C. In this case, the ratio of toluene to heptane may be 70 to 100 parts by weight of heptane or so based on 100 parts by weight of toluene.

Next, the crystals may be dried under reduced pressure at a temperature of 50° to 60° C. or so as occasion demands.

Thus, mirtazapine can be obtained.

EXAMPLES

Next, the present invention will be described more specifically on the basis of the examples, without intending to limit the present invention thereto.

Example 1

To 162 g of 1-butanol were added 60.93 g of potassium hydroxide and 40 g (0.1086 moles) of 2-(4-methyl-2-phenylpiperazin-1-yl)pyridine-3-carbonitrile oxalate, and the resulting mixture was heated at 125° to 135° C. As a result, it was confirmed by HPLC that the raw material 2-(4-methyl-2-phenylpiperazin-1-yl)pyridine-3-carbonitrile oxalate disappeared after about 7 hours passed from the addition.

Two-hundred grams of water was added to the reaction solution obtained above, and the mixture was allowed to separate into two layers at 40° to 50° C. The aqueous layer was further extracted with 34 g of 1-butanol. The butanol layers were combined together, and its pressure was reduced to 2.6 to 13 kPa. Thereafter, the mixture was concentrated at 40° to 60° C., to distill off 204 g of the solvent.

Next, 86 g of xylene was added to the resulting solution, and the mixture was subjected to azeotropic dehydration at an internal temperature of 125° to 135° C. When the water content of the mixture was reduced to 0.487% by weight (determined by Karl-Fischer method), the mixture was concentrated at 1350 to 140° C. under atmospheric pressure, to distill off 74 g of xylene and water.

There could be confirmed that the resulting compound was potassium 2-(4-methyl-2-phenylpiperazin-1-yl) pyridine-3-carboxylate from the finding that the retention time in HPLC and the infrared absorption spectrum (hereinafter referred as "IR") of the resulting compound were identical to those of separately prepared potassium 2-(4-methyl-2-phenylpiperazin-1-yl)pyridine-3-carboxylate. NMR and IR of the resulting potassium 2-(4-methyl-2-phenylpiperazin-1-yl)pyridine-3-carboxylate are as follows.

$^1$H-NMR (CDCl$_3$, 400 MHz) δ=2.00 (br, 1H), 2.10 (s, 3H), 2.32 (br, 1H), 2.53 (br, 1H), 2.85–2.87 (m, 1H), 3.25–3.33 (m, 2H), 3.65 (br, 1H), 5.65 (br, 1H), 6.39 (br,

1H), 6.78–7.52 (m, 5H), 8.09 (br, 1H) ppm IR (KBr) ν=1571, 1453, 1432, 1397, 1374, 759, 705 cm$^{-1}$ Reference Example Potassium 2-(4-methyl-2-phenylpiperazin-1-yl)pyridine-3-carboxylate obtained in Example 1 was formed into a free acid with hydrochloric acid, to give 2-(4-methyl-2-phenylpiperazin-1-yl)pyridine-3-carboxylic acid.

NMR and IR of the resulting 2-(4-methyl-2-phenylpiperazin-1-yl)pyridine-3-carboxylic acid are as follows.

$^1$H-NMR (CDCl$_3$, 400 MHz) δ=2.47 (s, 3H), 2.60–2.66 (m, 2H), 3.1–3.156 (m, 3H), 3.486–3.49 (m, 1H), 4.81–4.848 (d, 2H), 7.1–7.266 (m, 6H), 8.318–8.342 (m, 1H), 8.514–8.531 (m, 1H) ppm IR (KBr) ν=1571, 1456, 1429, 1386, 1136, 769 cm$^{-1}$ Example 2

Eighty-nine grams of THF was added to the reaction solution obtained in Example 1, to give a THF solution.

The THF solution was added in a thin stream to a solution prepared by dissolving 12.5 g of lithium aluminum hydride in 234 g of THF at 20° to 30° C. over 30 minutes, and the mixture was stirred at the same temperature for 3 hours and 30 minutes.

The disappearance of potassium 2-(4-methyl-2-phenylpiperazin-1-yl)pyridine-3-carboxylate was confirmed by HPLC, and 12.2 g of water was added in a thin stream thereto at 20° to 30° C. To the mixture were added 12.2 g of a 20% by weight aqueous sodium hydroxide and subsequently 38 g of water, and the mixture was heated for 1 hour.

The precipitated crystals were filtered, washed with 45 g of THF, and 375 g of THF was distilled off under atmospheric pressure.

Forty-two grams of heptane was added in a thin stream to the distilled residue at 48° to 49° C. over 30 minutes with stirring. The mixture was stirred at 0° to 5° C. for one hour, filtered at the same temperature, washed with a mixed solution of 43 g of toluene and 34 g of heptane, and dried, to give a compound as crystals (yield: 70.78%). There could be confirmed that the resulting compound was 2-(4-methyl-2-phenylpiperazin-1-yl)pyridine-3-methanol (21.78 g) from the finding that the above compound had the following physical properties:

Melting point: 124° to 126° C.;

$^1$H-NMR (δ: ppm): 8.16 (d, 1H, 2-H: pyridine), 7.36 (d, 1H, 4-H: pyridine), 7.29 (d, 2H, 2-H: phenyl), 7.13 (t, 2H, 3-H: phenyl), 7.07 (d, 1H, 4-H: phenyl), 6.88 (dd, 1H, 3-H: pyridine), 5.3 (br, 1H, OH), 4.86, 4.60 (d, 2H, CH$_2$—OH), 4.70 (dd, 1H, 2-H: piperazine), 3.18 (m, 2H, piperazine), 2.96 (m, 2H, piperazine), 2.46 (m, 1H, piperazine), 2.34 (m, 1H, piperazine), 2.37 (s, 1H, N—CH$_3$).

Example 3

To 822 kg of 1-butanol was added 309.5 kg of potassium hydroxide flake to dissolve, and 202.9 kg of 2-(4-methyl-2-phenylpiperazin-1-yl)pyridine-3-carbonitrile oxalate was added thereto at 30° to 50° C. in divided portions. The mixture was heated to 130° to 140° C., and stirred at the same temperature for 9 hours. The end point of the reaction was confirmed by HPLC, and thereafter the mixture was cooled to about 50° C., and 1014 kg of water was introduced thereinto. The mixture was stirred at 42° to 45° C., and the mixture was allowed to stand to separate into two layers.

To the aqueous layer was added 823.5 kg of 1-butanol at 40° to 47° C. with stirring, and the mixture was allowed to stand to separate into two layers. The organic layers were combined, and concentrated under reduced pressure until not less than 95% of 1-butanol used was distilled off. Thereafter, 436.9 kg of xylene was added to the concentrate, and the mixture was subjected to azeotropic dehydration at an internal temperature of 120° to 122° C. until its water content attained to not more than 1%. Further, the mixture was heated at atmospheric pressure to distill off 328 kg of a distillation fraction containing xylene. Thereto was added 430.6 kg of THF, to give a THF solution of potassium 2-(4-methyl-2-phenylpiperazin-1-yl)pyridine-3-carboxylate. Its water content was 179.5 ppm.

Example 4

To 889.15 kg of THF was added 65.6 kg of lithium aluminum hydride under nitrogen atmosphere, and the resulting solution was stirred for 2 hours. To this solution was added in a thin stream the THF solution of potassium 2-(4-methyl-2-phenylpiperazin-1-yl)pyridine-3-carboxylate obtained in Example 3 at 20° to 25° C. A vessel in which the potassium salt solution had been placed was washed with 21.4 kg of THF, and the resulting washing liquid was added to the reaction solution. The mixture was stirred at 23° to 25° C. for 3 hours. Thereafter, 62.6 kg of water was added in a thin stream thereto at 1° to 15° C., and 50.2 kg of a 25% by weight aqueous sodium hydroxide was added in a thin stream to the mixture at 4° to 15° C., and further 188.3 kg of water was added in a thin stream to the mixture at 10° to 20° C. The mixture was stirred at 20° to 25° C. for 70 minutes, and thereafter filtered, and aluminum hydroxide formed by hydrolysis of lithium aluminum hydride was washed with 903.5 kg of THF.

Under atmospheric pressure, 2535 L of THF was distilled off at an internal temperature up to 110° C., and 50 g of seed crystals of 2-(4-methyl-2-phenylpiperazin-1-yl)pyridine-3-methanol were added to the concentrate, and the mixture was stirred for 30 minutes. Thereto was added in a thin stream 215 kg of heptane at 50° to 65° C., and the mixture was cooled to 0° to 5° C., and aged for 1 hour. The mixture was filtered, and the crystals were washed with a solution prepared by mixing 110.5 kg of toluene with 87.1 kg of heptane and cooling the mixture to 0° to 5° C. The washed crystals were dried at 50° to 60° C., to give 124 kg of 2-(4-methyl-2-phenylpiperazin-1-yl)pyridine-3-methanol. Its yield [yield based on 2-(4-methyl-2-phenylpiperazin-1-yl)pyridine-3-carbonitrile oxalate] was 79.4%, and the HPLC purity was 99.7%.

The physical properties of the resulting 2-(4-methyl-2-phenylpiperazin-1-yl)pyridine-3-methanol are as follows.

Melting point: 120.6° to 121.6° C.; IR (KBr) ν=1573, 1429, 1128, 1036, 757.8, 701 cm$^{-1}$.

In addition, the microphotograph of the resulting 2-(4-methyl-2-phenylpipirazin-1-yl)pyridine-3-methanol is shown in FIG. 1.

Comparative Example 1

In 150 mL of THF was dissolved 10.2 g of 2-(4-methyl-2-phenylpiperazin-1-yl)pyridine-3-carboxylic acid under nitrogen atmosphere. To 300 mL of THF was added 10.2 g of lithium aluminum hydride, and the above THF solution was added in a thin stream to the mixture over 50 minutes under reflux. After refluxing the mixture for 4 hours, the mixture was cooled to 0° to 5° C., and 40.5 mL of water was gradually added in a thin stream thereto. Aluminum hydroxide was separated therefrom by filtration, and the filtrate was concentrated with an evaporator. The residue was allowed to recrystallize from an ether, to give 8.6 g of 2-(4-methyl-2-phenylpiperazin-1-yl)pyridine-3-methanol. Its yield was 98%.

Figure 2:
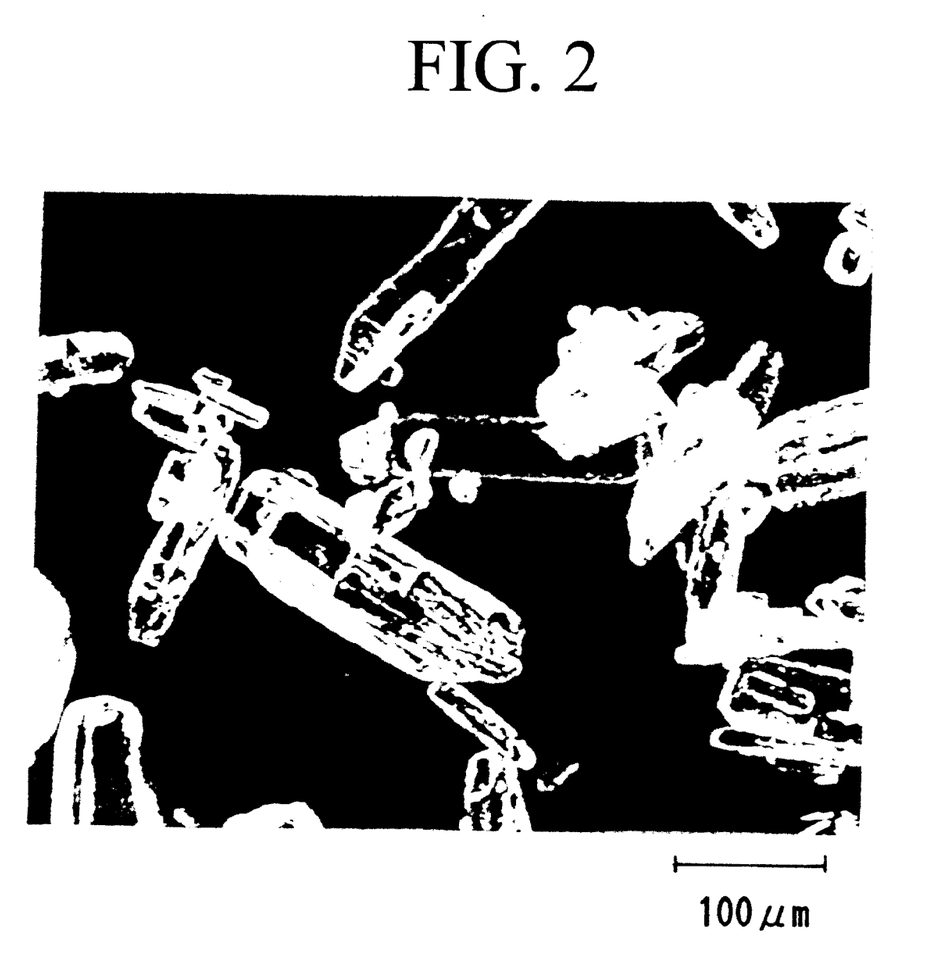
FIG. 2 is a microphotograph of 2-(4-methyl-2-phenylpiperazin-1-yl)pyridine-3-methanol obtained in Comparative Example 1.

The microphotograph of the resulting 2-(4-methyl-2-phenylpiperazin-1-yl)pyridine-3-methanol is shown in FIG. 2.

Example 5

To 442.6 kg of 98% concentrated sulfuric acid was added in divided portions 123 kg of 2-(4-methyl-2-phenylpiperazin-1-yl)pyridine-3-methanol over 3 hours at 5° to 32° C. under nitrogen atmosphere, and the mixture was stirred at 30° to 40° C. for 7 hours. The disappearance of the starting materials was confirmed by HPLC, and the resulting reaction solution was added in a thin stream to 885 kg of water at 0° to 30° C. The vessel in which the reaction solution had been placed was washed with 55 kg of sulfuric acid, and the resulting washing liquid was added to the hydrolyzed solution.

To the hydrolyzed solution was added in a thin stream 1285 g of a 25% aqueous sodium hydroxide at a temperature of 0° to 30° C. to adjust its pH to 1 to 2. To the resulting solution was added 6 kg of decolorizing carbon, and the mixture was stirred and filtered. The decolorizing carbon was washed with 118 kg of water. To the filtrate was added 159.1 kg of toluene, and the mixture was stirred at 20° to 30° C. for 15 minutes and allowed to stand to separate into two layers.

To the aqueous layer was added 159.1 kg of toluene, and 450.3 kg of a 25% aqueous sodium hydroxide was added to the mixture at 20° to 50° C. to adjust its pH to 11. The solution was heated to 75° to 80° C., and stirred for 15 minutes. The solution was allowed to stand for 90 minutes to separate into two layers. To the organic layer was added in a thin stream 126 kg of heptane at 50° to 60° C. over 65 minutes. The mixture was cooled to 0° to 5° C. over 3 hours and 40 minutes, and filtered. The resulting crystals were washed with a solution prepared by mixing 122.3 kg of toluene with 97 kg of heptane and cooling the mixture to 0° to 5° C. The crystals were dried at 50° to 60° C. under reduced pressure, to give 103.2 kg of mirtazapine. Its yield was 86.7%, and the HPLC purity was 99.8%.

Comparative Example 2

To 28 g of 2-(4-methyl-2-phenylpiperazin-1-yl)pyridine-3-methanol was added in a thin stream 100.8 g of 98% concentrated sulfuric acid at room temperature (25° to 30° C.) under nitrogen atmosphere. During the course of reaction, stirring became difficult, and the mixture partially heated up to near 50° C. The mixture was stirred at 30° to 40° C. for 2 hours. Since 8% of the intermediate still remained according to HPLC, the mixture was stirred for additional 6 hours. To the reaction solution was added 240 g of ice. As a result, the mixture heated up violently. Thereto was added 161 g of concentrated aqueous ammonia to make the solution alkaline (pH 9).

The solution was extracted with 200 mL of chloroform. The organic layer was dried over anhydrous magnesium sulfate, and concentrated with an evaporator. An ether was added to an oily residue with stirring to solidify the oily residue. The mixture was filtered. The residue was dried, and the solid products were re-crystallized from petroleum ether 40–60. However, the resulting solid products were pale yellow crystals having poor crystallinity and being in a state where the oil was partially solidified.

The crystals were filtered and dried, to give 20.1 g of pale yellow mirtazapine. Its yield was 76.6%, and the HPLC purity was 98.3%.

According to the process of the present invention, the pyridinemethanol compound represented by the formula (II) can be economically and efficiently prepared in a short period of time from the potassium pyridinecarboxylate represented by the formula (I). Also, according to the process of the present invention, the pyridinemethanol compound can be efficiently prepared in a short period of time from the pyridinecarbonitrile compound represented by the formula (I) or a salt thereof.

In addition, the mirtazapine can be favorably prepared form the pyridinemethanol compound.

EQUIVALENT

Those skilled in the art will recognize, or be able to ascertain using simple routine experimentation, many equivalents to the specific embodiments of the invention described in the present specification. Such equivalents are intended to be encompassed in the scope of the present invention as recited in the following claims.

What is claimed is:

1. A process for preparing a pyridinemethanol compound represented by the formula (II):

comprising the steps of:

(A) reacting a pyridinecarbonitrile compound represented by the formula (III):

or a salt thereof with potassium hydroxide in butanol, to give a potassium pyridinecarboxylate represented by the formula (I):

(B) adding water to the resulting reaction solution, and allowing the reaction solution to separate into an organic layer and an aqueous layer, thereby transferring the potassium hydroxide contained in the reaction solution to the aqueous layer;

(C) separating the organic layer from the layer; and (D) adding a metal hydride to the organic layer to reduce the potassium pyridinecarboxylate with the metal hydride.

2. The process according to claim 1, further comprising the steps of:

(E) adding butanol to the organic layer obtained in the step (C);

(F) allowing to separate into a butanol layer and an aqueous layer to transfer the potassium pyridinecarboxylate existing in the aqueous layer to the butanol layer;

(G) combining the organic layer with the butanol layer to give a liquid mixture; and (H) using the liquid mixture in place of the organic layer of the step (D).

3. The process according to claim 2, further comprising the steps of:

(I) distilling away the butanol and water from the liquid mixture obtained in the step (G); and (J) using the liquid mixture in place of the liquid mixture in the step (H).

4. The process according to claim 2, further comprising the steps of:

(K) mixing the liquid mixture obtained in the step (C) with a hydrocarbon;

(L) heating the resulting solution to azeotropically distill away the butanol and water; and (M) using the resulting mixture in place of the liquid mixture of the step (H).

5. The process according to claim 1, wherein said butanol is 1-butanol, isobutanol, or a mixture thereof.

6. The process according to claim 1, wherein said butanol is 1-butanol.

7. The process according to claim 1, wherein the amount of butanol is 300 to 800 parts by weight based on 100 parts by weight of the pyridinecarbonitrile compound or a salt thereof.

8. The process according to claim 1, wherein said potassium hydroxide is flaky or granular.

9. The process according to claim 1, wherein the amount of the potassium hydroxide is 7 to 14 moles per one mole of the pyridinecarbonitrile compound or a salt thereof.

10. The process according to claim 1, wherein the reaction temperature of the pyridinecarbonitrile compound or a salt thereof with potassium hydroxide is 120° to 145° C.

11. The process according to claim 1, wherein the amount of water added in the step (B) is 400 to 600 parts by weight based on 100 parts by weight of the pyridinecarbonitrile compound or a salt thereof.

12. The process according to claim 1, wherein the reaction solution is separated into the organic layer and the aqueous layer at a temperature of 30° to 60° C. in the step (B).

13. The process according to claim 3, wherein the butanol and water are distilled away under reduced pressure in the step (I).

14. The process according to claim 13, wherein the pressure during distillation is 1 to 20 kPa.

15. The process according to claim 13, wherein the temperature during the distillation of butanol and water is 30° to 80° C.

16. The process according to claim 4, wherein the hydrocarbon used in the step (K) is toluene, xylene, or benzene.

17. The process according to claim 4, wherein the hydrocarbon used in the step (K) is xylene.

18. The process according to claim 4, wherein the amount of the hydrocarbon used in the step (K) is 100 to 600 parts by weight based on 100 parts by weight of the pyridinecarbonitrile compound or a salt thereof.

19. The process according to claim 4, wherein the temperature during the azeotropic distillation in the step (L) is 110° to 130° C.

20. The process according to claim 4, wherein the azeotropic distillation is carried out until the water content in the solution attains not more than 1% by weight in the step (L).

* * * * *